(12) United States Patent
Latkany

(10) Patent No.: US 7,490,938 B2
(45) Date of Patent: Feb. 17, 2009

(54) METHOD, DEVICE AND COMPUTER PROGRAM FOR SELECTING AN INTRAOCULAR LENS FOR AN APHAKIC EYE THAT HAS PREVIOUSLY BEEN SUBJECTED TO REFRACTIVE SURGERY

(76) Inventor: Robert Adam Latkany, 115 E. 57th St., 10th Floor, New York, NY (US) 10022

( * ) Notice: Subject to any disclaimer, the term of this patent is extended or adjusted under 35 U.S.C. 154(b) by 972 days.

(21) Appl. No.: 10/923,466

(22) Filed: Aug. 20, 2004

(65) Prior Publication Data

US 2005/0177313 A1    Aug. 11, 2005

Related U.S. Application Data

(60) Provisional application No. 60/543,121, filed on Feb. 9, 2004.

(51) Int. Cl.
*A61F 2/16* (2006.01)

(52) U.S. Cl. .................... 351/177; 623/6.11
(58) Field of Classification Search .............. 351/177; 623/6.11–6.62
See application file for complete search history.

(56) References Cited

U.S. PATENT DOCUMENTS 5,968,095 A * 10/1999 Norrby ................. 128/898

* cited by examiner

*Primary Examiner*—Darryl J Collins
(74) *Attorney, Agent, or Firm*—Law Offices of Albert Wai-Kit Chan, PLLC

(57) ABSTRACT

A method for selecting an intraocular lens for an aphakic eye that has previously been subjected to refractive surgery by calculating the required power of an IOL to provide the desired refraction using a known formula, and then applying an adjustment based upon the spherical equivalence of the eye prior to refractive surgery.

16 Claims, 5 Drawing Sheets

Figure 1:
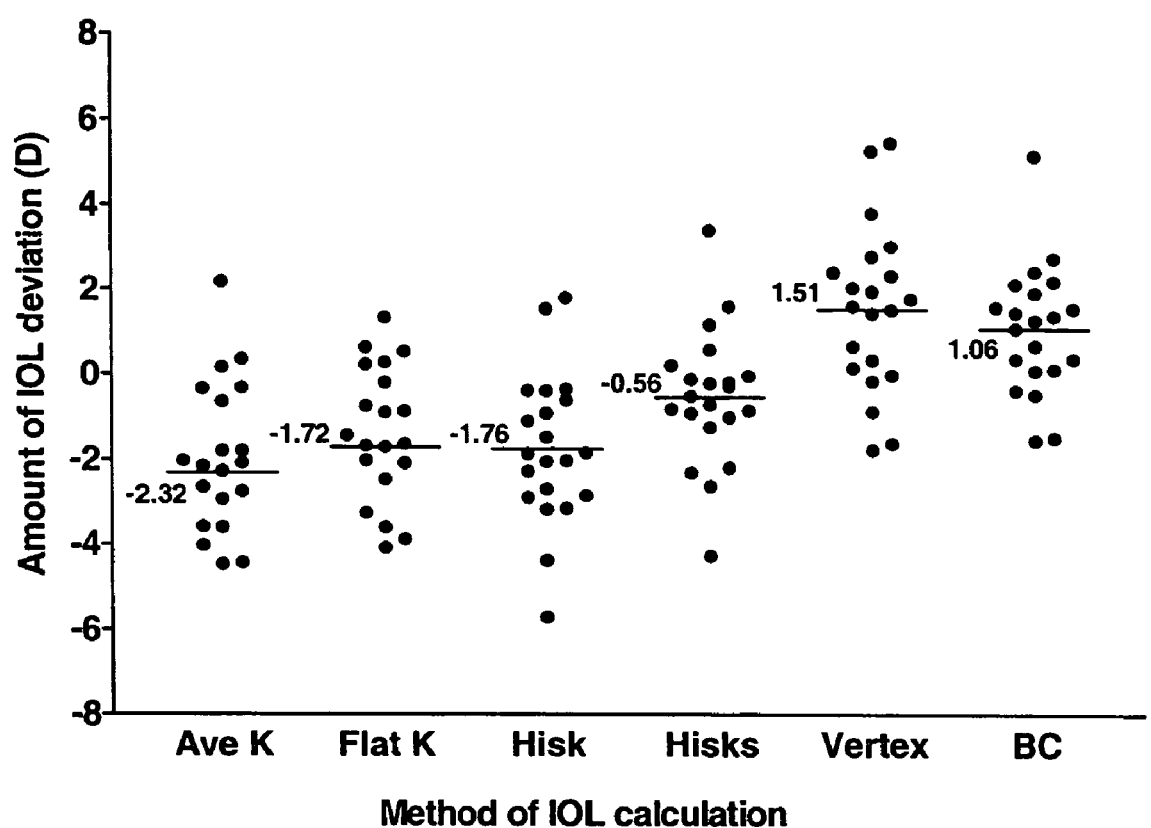

METHOD, DEVICE AND COMPUTER PROGRAM FOR SELECTING AN INTRAOCULAR LENS FOR AN APHAKIC EYE THAT HAS PREVIOUSLY BEEN SUBJECTED TO REFRACTIVE SURGERY

This application claims benefit of U.S. Ser. No. 60/543,121, filed Feb. 9, 2004, the contents of which are incorporated herein by reference in its entirety.

FIELD OF THE INVENTION

The present invention relates to a method, device and computer program for deriving a more accurate intraocular lens power suitable for a patient previously subjected to refractive surgery.

BACKGROUND OF THE INVENTION

Publications referred to throughout this application are hereby incorporated by reference into this application in their entireties to more fully describe the state of the art to which this invention pertains.

the posterior surface is not altered. Changes in this relationship account for errors in traditional keratometry readings and this error becomes increasingly significant with higher corrections (8, 13, 15, 22).

Our study supports both of these findings. For myopic eyes, both $IOL_{flatK}$ and $IOL_{avgK}$ are based on post-LASIK keratometry readings, and both result in under correction (−1.13 and −0.92 respectively). Also, each of these methods was further deviant for higher amounts of pre-LASIK myopia. These deviations were statistically significant (p=0.0036 and p=0.0094, respectively). Conversely, for hyperopic eyes $IOL_{avgK}$ and $IOL_{steepK}$ resulted in overcorrection (1.36 and 0.75). Furthermore these 2 methods showed a tendency to further overcorrect for increasing amounts of pre-refractive surgery hyperopia, however this was not statistically significant.

Currently the most widely used method for keratometric calculation post refractive surgery is the clinical history method. Table 1 below shows a review of the current case series and reports in the literature. Most of these series used the clinical history method and found it the most accurate of the different methods of determining central corneal power. Accurately calculating this method can pose some challenges.

TABLE 1

Review of Case Series/Reports
Summaries of case series of cataract surgeries following excimer refractive surgery

| Author | Year | Cases | Method of calculation | Findings/Suggestions |
| --- | --- | --- | --- | --- |
| Argento et al.9 | 2003 | 7 | Multiple | Clinical history method most reliable |
| Odenthal et al (12) | 2002 | 15 | Multiple combined with Hoffer Q | Clinical history method most reliable, |
| Randleman et al. (16) | 2002 | 10 | Multiple method, and average of 2 | Clinical history method, contact lens |
| Ladas et al. (17) | 2001 | 2 | Topography lens | Hyperopic result, needing piggyback |
| Gimbel et al. (19) | 2001 | 6 | Clinical History, Manual than manual keratometry | Clinical history method more reliable |
| Gimbel et al. (20) | 2000 | 5 | Clinical History, Manual flattest K most reliable | Clinical History method or use of |
| Kalski et al (21) | 1997 | 4 | Multiple | Clinical history method most reliable |
| Case Reports | | | | |
| Lesher, et al. (23) | 1994 | 1 | Manual keratometry | Hyperopic Result (+1.60) |
| Morris, et al. (24) | 1998 | 1 | Manual keratometry | Hyperopic Result (+4.50) |

With the popularity of refractive surgery rising, calculating intraocular lens (IOL) power after refractive surgery is becoming increasingly important. The calculation is often incorrect because of the difficulty in obtaining an accurate central corneal power in a post-refractive surgery patient. The measured keratometric values for previously myopic patients are usually higher than the actual power, leading to hyperopic results. Conversely, the measured keratometric values for previously hyperopic patients are usually lower than the actual power, leading to a myopic result. Both inaccuracies lead to an inability to meet our patient's rising expectations.

Figure 2:
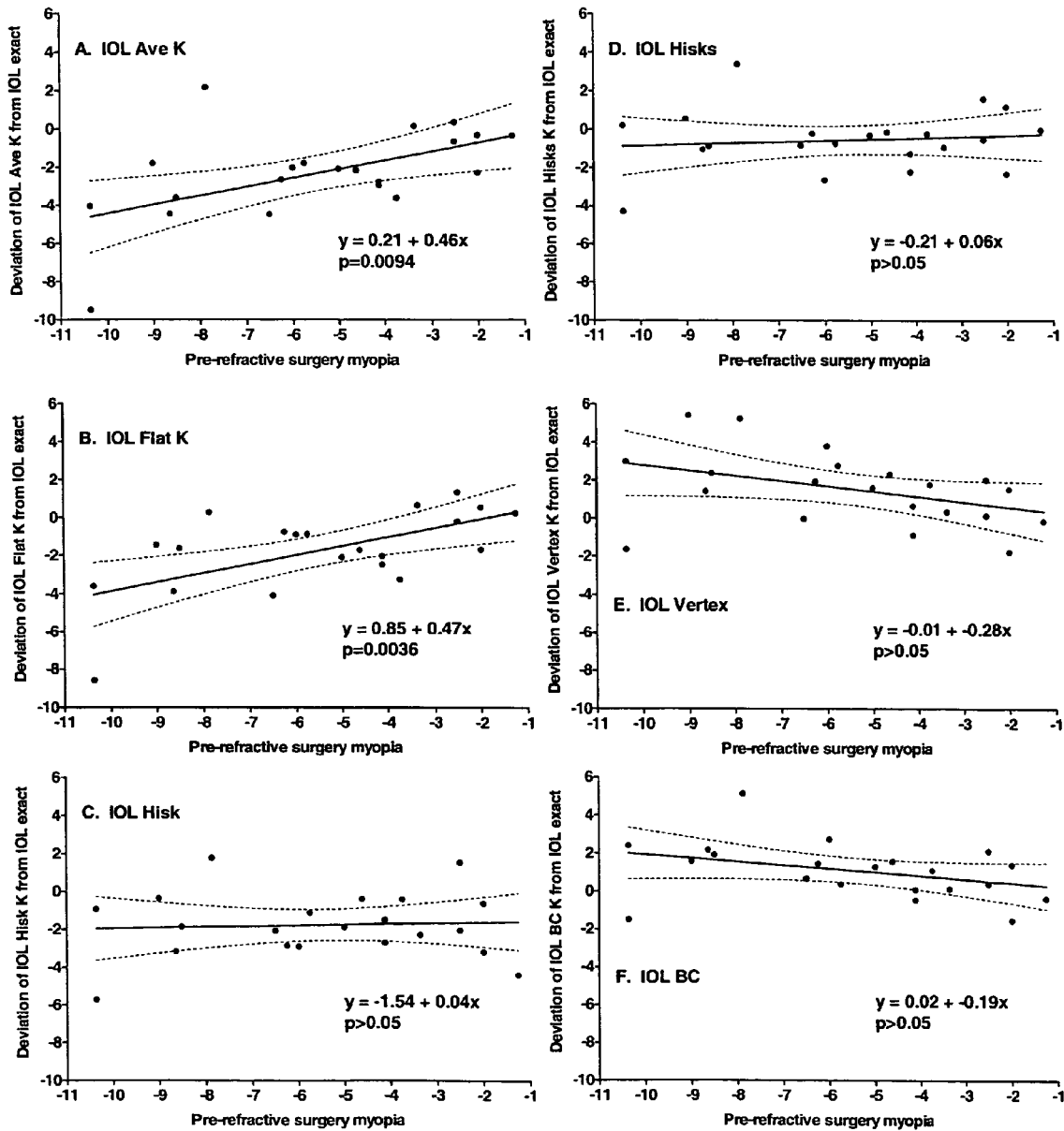
Figure 3:
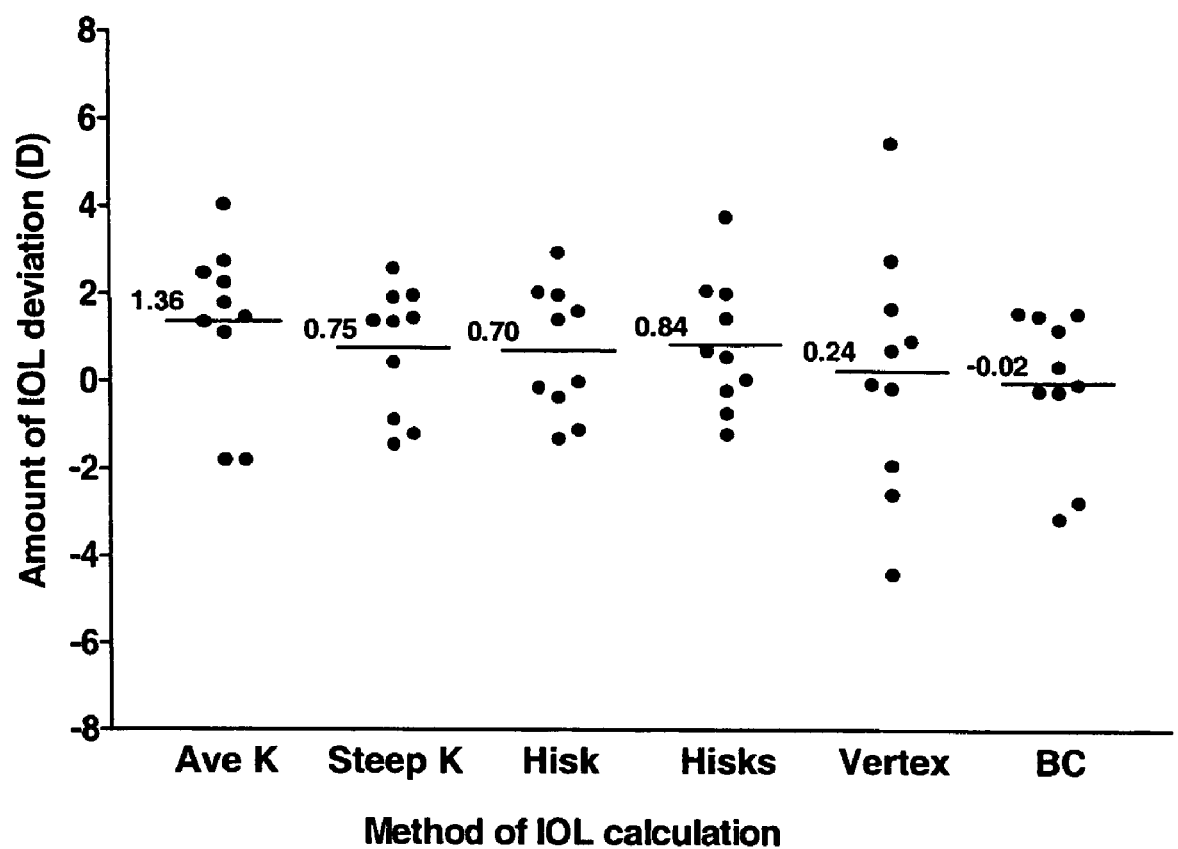

Intraocular lens power calculations in eyes with previous refractive surgery remains difficult largely due to the inaccuracy of traditional keratometry measurements. Keratometry readings which are steeper than actual values which occur in previously myopic eyes lead to underestimation of IOL power and a hyperopic result. Keratometry readings which are flatter than actual values which occur in previously hyperopic eyes lead to overestimation of IOL power and a myopic result. Traditional keratometers do not account for the asphericity of the cornea and after refractive surgery the asphericity of the cornea decreases. The anterior curvature changes while The pre-cataract extraction SEQ is a value needed to determine the total change in SEQ caused by refractive surgery. Error can be encountered when myopia induced by nuclear sclerosis is incorporated into this value, leading to inaccurate change in SEQ and error in IOL power calculation. For example, in our study, after refractive surgery the difference in mean SEQ prior to cataract formation and after cataract formation was −1.09. Therefore, it is important to account for myopia induced by nuclear sclerosis. Variations in clinical history method include keeping the SE at the corneal versus the spectacle plane. Studies have shown that using the spectacle plane refractions in the clinical history method are more accurate (11, 12, 17). Our study also shows this for myopic patients, as the mean deviation of $IOL_{HisK}$ from $IOL_{exact}$ was −1.76D whereas the mean deviation of $IOL_{HisKs}$ from IOL exact was only −0.56D. For hyperopic patients the difference between $IOL_{HisK}$ and $IOL_{HisKs}$ from $IOL_{exact}$ was similar (0.70D and 0.84D, respectively). Finally, this method assumes that there is a one to one relationship between change in refraction and change in central corneal power, which may not hold for higher refractive corrections (13). Our study shows that there is a tendency for $IOL_{HisK}$ and $IOL_{HisKs}$ to be more inaccurate with increasing amounts of pre-refractive surgery myopia and hyperopia (FIGS. 2 and 3). However these deviations are not statistically significant.

Alternative methods for corneal power calculations include the contact lens method. This is determined by the difference in manifest refraction before and after insertion of a plano hard contact lens with a known base curve. The change in refraction is subtracted from the known base curve and this is assumed to be the curvature of the central cornea (2). This method was evaluated for patients with normal corneas with and without cataracts and was found to be accurate in patients with vision as low as 20/80 due to cataracts (3). The corneal power calculation becomes unreliable when visual acuity is less than 20/80. Other issues involved in the contact lens method in post refractive surgery patients include adequate hard contact lens fit.

Both of these above methods rely on either pre-refractive surgery measurements and/or pre-cataract surgery measurements. If these are unavailable the current options for measuring central corneal power include conventional keratometry (CK) (either automated or manual) or corneal topography (CT). Studies have shown that measurements obtained on post surgical patients with corneal topography are more accurate than conventional keratometry (4-7). This result is likely due to the fact that corneal topography measures over 1000 points in the central 3.0 mm zone, while conventional keratometry only measure 2 points located 3.2 mm and 2.6 mm from the corneal center.

Unfortunately, both CK and CT calculate the average corneal power using an effective index of refraction of 1.3375. This value assumes an almost spherical relationship of the cornea and a constant difference between the anterior and posterior curvature. In refractive surgery this value is not reliable as ablation changes curvature principally on the anterior surface and the posterior surface is changed to a lesser extent. Measurement of the posterior corneal curvature remains difficult. Also, how the posterior curvature changes after refractive surgery remains controversial. One study by Seitz, et al showed a mean increase in posterior curvature of 0.11D in 57 eyes following myopic LASIK. Furthermore, the higher the attempted correction, the more of an increase in posterior curvature (10).

Newer methods of measuring corneal topography are becoming available, which might make measuring keratometry post refractive surgery more reliable. These include pan corneal scanning slit-beam topography, stereoscopic topography (14). Once a more accurate measurement of posterior surface curvature is available, it would also be possible to use Gaussian optics formula to better estimate the total power of the central cornea.

The vertex IOL power is another method to estimate IOL calculations in post refractive surgery patients. A study by Feiz et al. examined this method, where the IOL power for emmetropia is based on pre-LASIK keratometry values (13). The spherical equivalent change due to LASIK was then used to modify the IOL power, assuming a diopter of change in IOL produced only 0.7 diopter change in refraction at the spectacle plane. This is based on the IOL position behind the iris and with a vertex distance of 12-13 mm. This method produced higher IOL powers post myopic LASIK and lower IOL powers post hyperopic LASIK. Further, the higher the amount of treatment the more inaccurate traditional keratometry readings would be. Based on their results, this study created a nomogram based on linear regression analysis.

A study by Hamed et al. showed that post refractive surgery keratometry readings (either conventional or topography) could be modified to estimate corneal power. Specifically, using the EyeSys Corneal Analysis system, the authors recommend that the corneal power should be reduced by 15% of the total refractive change induced by surgery. If standard keratometry is used, this value should be reduced by 24%. This study found that standard keratometry was less accurate than the value obtained by the EyeSys (8). Both of these studies present new theories on predicting IOL power post refractive surgery based on manual keratometry and/or topography readings. Actual clinical results have not been reported.

In our study the vertex IOL and a back calculated IOL methods were analyzed. For myopic eyes, both methods interestingly produced an IOL which was stronger on average than IOL exact (1.51D and 1.06D, respectively), unlike the other methods which produced under corrected IOL. Also, these two methods showed a trend toward increased overcorrection from the intended power for higher amounts of pre-refractive surgery myopia; however it did not achieve statistical significance. For the hyperopic group, these two methods calculated an overcorrected IOL as well (0.14D and 0.58D, respectively) and showed a tendency to further overcorrect for higher amount of hyperopia.

Overall, for the myopic group, $IOL_{HisKs}$ produced the most accurate results followed by $IOL_{BC}$, $IOL_{vertex}$, $IOL_{flatK}$, $IOL_{HisK}$ and finally $IOL_{AvgK}$ when compared to $IOL_{exact}$ which would theoretically have given an emmetropic result. Of note there was no statistical difference between $IOL_{HisKs}$ and $IOL_{exact}$ for myopic eyes. For the hyperopic group, $IOL_{vertex}$ was most accurate, followed by $IOL_{BC}$, $IOL_{HisK}$, $IOL_{HisKs}$, $IOL_{SteepK}$, and finally $IOL_{AvgK}$. For this group only $IOL_{vertex}$ and $IOL_{BC}$ showed no statistical difference to $IOL_{exact}$. Based on these results we would recommend using $IOL_{HisKs}$ method for previously myopic eyes, and $IOL_{BC}$ or $IOL_{vertex}$ for previously hyperopic eyes.

When using $IOL_{HisK}$, $IOL_{HisKs}$, $IOL_{vertex}$, and $IOL_{BC}$ it is necessary to obtain pre-refractive surgery data, which includes manifest refraction and keratometry. Unfortunately, this data is not always present. If not present, a practitioner would have to rely on the $IOL_{avgK}$ or $IOL_{flatK}$ (myopic eyes)/$IOL_{steepK}$ (hyperopic eyes). Our study shows that using these values without an adjustment would produce a large under correction for myopic eyes and a large overcorrection for hyperopic eyes. In our study there was a statistically significant linear regression of deviation of $IOL_{flatK}$ (p=0.0036) and $IOL_{avgK}$ (p=0.0094) to pre-refractive surgery $SEQ_m$. Based on this regression a more accurate IOL power can be predicted. For $IOL_{flatK}$ a prediction for adjustment would be: $-(0.47x+0.85)$ where x=pre-refractive surgery $SEQ_m$. In this situation only pre-refractive surgery $SEQ_m$ needs to be known, which is usually easier to obtain from the patient (old pair of glasses) than the entire pre-refractive surgery data. Using paired t-test, the adjusted $IOL_{flatK}$ was found to have no statistical difference to $IOL_{exact}$, and thus can be used an new formula to predict more accurate IOL powers. An adjustment to $IOL_{avgK}$ was found to be statistically significant as well, and this may prove to be useful once further prospective data can be used.

A Clinical Example would be as Follows:

Pre-refractive surgery myopic spherical equivalent ($SEQ_m$): $-6.50$ D

Flattest keratometry reading: 42.18 D

Using flattest keratometry reading into SRK/T formula IOL for emmetropia calculated $IOL_{FlatK}$: 17.76 D Adjustment based on pre-refractive surgery $SEQ_m$:

Adjustment of $IOL_{flatK}=-(0.47x+0.85)$ (x=pre-refractive surgry $SEQ_m$)

$-(0.47(-6.5)+0.85)$ $+2.20$

Adjusted $IOL_{flatK}=17.76+2.20=19.96$ D

Based on this example, the adjusted IOL would provide a more accurate result post-operatively.

For hyperopic eyes, linear regression was performed on all methods compared to pre-refractive surgery hyperopia. The only statistically significant relationship was $IOL_{vertex}$ (P=0.021). This data, however, requires pre-operative keratometry and manifest refraction is still needed for this method.

A clinical example of an adjustment to $IOL_{vertex}$ based on pre-refractive surgery $SEQ_h$ is as follows:
Pre-refractive surgery $SEQ_h$: +2.00
$IOL_{vertex}$: 20.00
Adjustment of $IOL_{vertex}$: $-(-0.80x+2.69)$ where x=pre-fractive surgery $SEQ_h$ $-(-0.80(2.00)+2.69)$ $-1.09$ $IOL_{vertex}$ +Adjustment: 20.00 D−1.09 D 18.91D

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

According to a broad aspect of the invention, a method is disclosed for selecting an intraocular lens for an aphakic myopic or hyperopic eye by calculating the required power of an IOL to provide the desired refraction using a known formula and by adjusting the calculated IOL power by subtracting a value based upon the pre-refractive surgery spherical equivalent of the eye, or SEQ, and its relationship to the calculated and exact IOL powers.

According to another broad aspect of the invention, a computer program employing the above method for selecting an intraocular lens for an aphakic eye is disclosed.

According to another broad aspect of the invention, a electronic or mechanical calculating device employing an above method for selecting an intraocular lens for an aphakic eye is disclosed. Moreover, the electronic calculating device utilizes a computer program which employs the above-described method for selecting an intraocular lens for an aphakic eye.

DETAILED DESCRIPTION OF THE FIGURES

FIG. 1. Scatter plot of deviation from emmetropia of each IOL calculation method for myopic eyes FIG. 2. Graph showing linear regression of IOL calculation methods to pre-refractive surgery $SEQ_m$. The trends for $IOL_{avgK}$ and $IOL_{flatK}$ are statistically significant FIG. 3. Scatter plot of deviation from emmetropia of each IOL calculation method for hyperopic eyes FIG. 4. Graph showing linear regression of IOL calculation to pre-refractive surgery $SEQ_h$. $IOL_{vertex}$ showed statistical significance FIG. 5. Flow chart of the method of this invention for selecting an intraocular lens for an aphakic eye

DETAILED DESCRIPTION OF THE INVENTION

This invention provides a method of selecting an intraocular lens for an aphakic eye, comprising: calculating the required power of an IOL to provide the desired refraction using a known formula; and adjusting the calculated IOL power by subtracting a value based upon the pre-refractive surgery spherical equivalent of the eye, or SEQ, and its relationship to the calculated and exact IOL powers.

Figure 5:
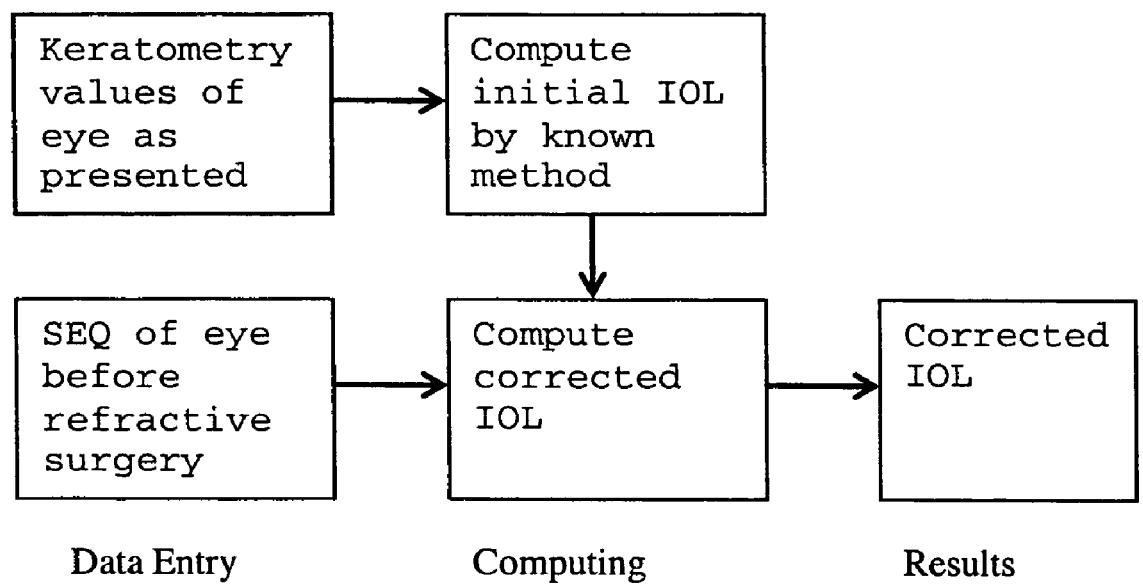

FIG. 5 is a flow chart of the operations to select an intraocular lens for an aphakic eye, using the method of this invention. The keratometry values obtained for the eye as presented are used to compute an initial IOL by a known method, as described in more detail below. The SEQ for the eye before refractive surgery was performed is then used with the initial IOL to compute a corrected IOL by the method described in more detail below. The steps of computing the initial and corrected IOL can be performed concurrently or sequentially with a common computing device or separate devices. The vision correction provided by a lens with the corrected IOL provides improved vision correction compared with a lens having the initial IOL computed by other known methods. The computing steps can be performed by "pencil and paper" calculations using the known formulas and the formulas provided by this invention. However, the calculations can be performed faster, easier and more accurately by using a computing device. A mechanical computing device, such as a slide rule, can be used, or various forms of electronic computers electronic computing devices can be used. When an electronic computing device is used, the computing steps can be made automatically by providing a computer program that will perform the steps in FIG. 5 when the basic data are entered.

This invention provides a method for selecting an intraocular lens for an aphakic myopic eye, comprising: calculating the required power of an IOL to provide the desired refraction using the known SRK/T formula using the flattest keratometry reading; and adjusting the calculated power by subtracting a value equal to $a(SEQ_m)+b$. Where $SEQ_m$ is the pre-refractive surgery spherical equivalent of the myopic eye and a and b are slope and intercept constants respectively derived from regression analysis of the relationship of $SEQ_m$ to the deviation of the calculated IOL power from the exact IOL power. In an embodiment of the above method, the value of a is between 0.4 and 0.6 and the value of b is between 0.75 and 0.85. In another embodiment, the value of a is 0.47 and the value of b is 0.8.

This invention provides a method for selecting an intraocular lens for an aphakic myopic eye comprising: calculating the required power of an IOL to provide the desired refraction using the known SRK/T formula using the average keratometry reading; and adjusting the calculated power by subtracting a value equal to $a(SEQ_m)+b$. Where $SEQ_m$ is the pre-refractive surgery spherical equivalent of the myopic eye and a and b are slope and intercept constants respectively derived from regression analysis of the relationship of $SEQ_m$ to the deviation of the calculated IOL power from the exact IOL power. In an embodiment of the above method, the value of a is between 0.4 and 0.6 and the value of b is between −0.5 and 1.0. In another embodiment, the value of a is 0.46 and the value of b is 0.21.

This invention provides a method for selecting an intraocular lens for an aphakic hyperopic eye, comprising: calculating the required power of an IOL to provide the desired refraction using the known Vertex formula; and adjusting the calculated power by subtracting a value equal to $a(SEQ_h)+b$. Where $SEQ_h$ is the pre-refractive surgery spherical equivalent of the hyperopic eye and a and b are slope and intercept constants respectively derived from regression analysis of the relationship of $SEQ_h$ to the deviation of the calculated IOL power from the exact IOL power. In an embodiment of the above method, the value of a is between 0.6 and 1.0 and the value of b is between 1.7 and 3.7. In a separate embodiment, the value of a is 0.8 and the value of b is 2.69.

This invention provides computer programs employing the above methods for selecting an intraocular lenses for aphakic eyes.

This invention provides calculating devices employing the above methods for selecting intraocular lenses for aphakic eyes. In an embodiment, the calculating device is electronic or mechanical. In another embodiment the electronic calculating device contains a computer program employing an above method for selecting intraocular lenses for aphakic eyes.

EXAMPLE 1

Patients and Experimental Methods

The results of 31 eyes that underwent phacoemulsification with IOL implantation following Laser Assisted In-Situ Keratomileusis (LASIK) were studied retrospectively. All 31 eyes had LASIK, 21 of which were myopic treatments and 10 of which were hyperopic treatments.

The LASIK procedure was performed as previously described.[1] A flap was created by the Moria (Doylestown, Pa.) microkeratome or Automated Corneal Shaper (Rochester, N.Y.) microkeratome. Excimer laser ablation was performed by either the VISX (Santa Clara, Calif.) or Alcon Ladarvision (Fort Worth, Tex.) laser. The procedures were uncomplicated and no sutures were used.

Phacoemulsification cataract surgery procedure was done in all cases. A temporal corneal incision was made and a circular capsulorhexis was created. Phacoemulsification was completed after hydrodissection. Implantation of an IOL within the bag was then completed. Each procedure was uncomplicated.

IOL power was calculated using SRK/T (Sanders, Retzlaff, Kraff) formula. The keratometry values used in the SRK/T were calculated by clinical history method in 24/31 cases, and videokeratography in 4/31 cases. In 3/31 cases the IOL power was back calculated based on pre-LASIK keratometry readings, and adjusted for the amount of LASIK treatment. Each of these methods are described below. The targeted post-phacoemulsification power was plano. The choice of IOL power was based on the surgeon's preference. The IOL used was either SA60AT (Alcon Inc., Ft. Worth, Tex.) (18 cases), AQ2010V (STAAR Surgical, Monrovia, Calif.) (11 cases), or LI61U (Bausch and Lomb, San Dimas, Calif.) (2 cases).

The IOL power to achieve emmetropia was calculated using each of the following methods for all patients:

Method I:

The clinical history method as described by Holladay[25] and Guyton et al[26] was used to determine the refractive corneal power (His K). The change in spherical equivalent from refractive surgery was determined and adjusted for the corneal plane. This change was then subtracted from pre-LASIK keratometry readings in myopic eyes and added to pre-LASIK keratometry readings in hyperopic eyes. The corneal power derived from this method was used in the SRK/T formula to determine an IOL for emmetropia ($IOL_{HisK}$).

Method II:

The clinical history method as described in Method I was used to determine the corneal power with an adjustment. The change in spherical equivalent after refractive surgery was not adjusted for the corneal plane and was left at the spectacle plane ($HisK_s$). This change was then subtracted from pre-LASIK keratometry readings in myopic eyes, and added to pre-LASIK keratometry readings in hyperopic eyes. The corneal power derived from this method was used in the SRK/T formula to determine an IOL for emmetropia ($IOL_{HisKs}$).

Method III:

The IOL power for emmetropia was determined based on pre-LASIK keratometry readings by the SRK/T formula. This theoretical IOL was adjusted to the change in spherical equivalent with the following assumptions:

1. The change in spherical equivalent was balanced by the change in IOL power
2. Each diopter of IOL change was equivalent to 0.7 change in spherical equivalent at the spectacle plane, which is due to the change in vertex distance from the spectacle plane (12-13 mm) to the position of the IOL behind the iris.

This is the same method used in an article by Feiz et al.[13] and will be referred to as $IOL_{vertex}$.

Method IV:

Similar to Method III, IOL powers were calculated based on pre-LASIK keratometry readings by the SRK/T formula. The IOL chosen was that which was back calculated and aimed for the pre-LASIK spherical equivalent ($IOL_{BC}$).

Method V:

An IOL was chosen based on average post-LASIK keratometry reading ($IOL_{avgK}$).

Method VI:

An IOL was chosen based on flattest post-LASIK keratometry reading ($IOL_{flatK}$) in previously myopic eyes or the steepest keratometry reading ($IOL_{steepK}$) in previously hyperopic eyes.

For methods V and VI the keratometry readings were taken after the LASIK procedure and were inserted into the SRK/T formula to derive an IOL for emmetropia.

For each patient a theoretical keratometry reading was determined which reflected the real refractive power of the cornea. This was determined by repeatedly entering K values into the SRK/T formula, while keeping all other constants the same (IOL power, Axial Length, and A-constant), until a K value would achieve the patient's post cataract surgery refraction ($K_{exact}$). The $K_{exact}$ was then used in the SRK/T formula to determine an IOL for emmetropia ($IOL_{exact}$), Theoretically, the $IOL_{exact}$ would have achieved emmetropia in each patient. Each of the IOL powers derived from the 6 methods were compared to $IOL_{exact}$. We compared the mean differences between each of IOL power calculation after refractive surgery and IOL exact measurement and determined statistical significance by paired t-test. In addition, we calculated the percentages of change of IOL power calculation from IOL exact measurement. This calculation would help to get the magnitude and direction in change for IOL power calculations.

Also, the difference between each method against the $IOL_{exact}$ was plotted against the amount of spherical equivalent change from LASIK and then analyzed using linear regression. This would determine if the amount of LASIK correction would influence the IOL power chosen.

Case Example:

A 40 year old male presented with a visually significant nuclear cataract in the left eye. Two years prior the patient had successful LASIK to correct myopia. The following are pre- and post-LASIK data:

Pre-LASIK spherical equivalent: −7.87

Post-LASIK spherical equivalent, before developing cataract: −0.75

Pre-LASIK average keratometry: 43.33

Post-LASIK average keratometry: 39.00

Post-LASIK flattest keratometry reading: 38.37

Axial length: 26.83

IOL type: SA60AT, A-constant 118.4

Method I

First a corneal power is determined:

Conversion of spherical equivalent (SEQ) from spherical to corneal plane

Pre-LASIK SEQ on spectacle plane ($SEQ_s$)=−7.87

Pre-LASIK SEQ on corneal plane=1000/((1000/SEQ)−14 (Vertex dist))

$$SEQ_c = 1000/((1000/-7.87)-14)$$

$$= -7.09$$

Post-LASIK SEQ on spectacle plane (SEQ$_s$)=−0.75
Post-LASIK SEQ on corneal plane=1000/((1000/SEQ)−14)

$SEQ_c = -0.74$

Change in $$SEQ_c = \text{Pre-LASIK } SEQ_c - \text{Post LASIK } SEQ_c$$

$$= -7.09 - (-0.74)$$

$$= -6.37$$

Calculation of His K=Pre-LASIK Keratometry−change in SEQ$_c$

=36.98

His K was entered into SRK/T to determine IOL-
$_{HisK}$=18.16

Method II
Change in SEQ kept at spectacle plane=Pre-LASIK SEQ$_s$−Post-LASIK SEQ$_s$

=−7.87−(−0.75)

=−7.12

Calculation of HisKs=Pre-LASIK keratometry−change in SEQ$_s$

=35.46

His Ks was entered into SRK/T to determine IOL$_{HisKs}$=19.75

Method III
An IOL was calculated using SRK/T based on Pre-LASIK keratometry=10.37.

For the correct IOL, the power must be balanced the amount of change in spherical equivalent change from LASIK, furthermore every IOL diopter change only changes the spherical equivalent by 0.7:

$$IOL_{vertex} = 10.37 + (7.87/0.7)$$

$$= 21.61$$

Method IV
IOL powers were calculated using SRK/T based on Pre-LASIK Keratometry. The IOL chosen is that which aims for the original spherical equivalent.

$IOL_{BC}$=21.50

Method V
IOL power was calculated using Avg K (39.00 D)

$IOL_{avgK}$=15.73

Method VI
IOL power was calculated using Flattest K (38.37 D)

$IOL_{flatK}$=16.64.

Results

The mean age of the 13 men and 9 women was 55.82±9.56 (SD) (Range 42-77). The cohort was divided into a myopic and hyperopic group. For the myopic group, the mean spherical equivalent (SEQ) prior to refractive surgery was −5.45±2.82 D (Range [−10.37]−[−1.25]). The mean SEQ after refractive surgery prior to cataract formation was −0.23±0.90 D (Range [+1.25]−[−3.62]D). After cataract development, mean SEQ was −1.88±1.59 D (Range [−5.13]−[+1.25]D), with a mean BCVA 0.59±0.20 (20/30). After cataract surgery, the mean post-op SEQ was +1.48±2.09 D (Range [−2.28]−[+6.30]D) off the aim of the IOL. The mean SEQ after cataract surgery was +0.03±2.44 D (Range [−3.12]−[+7.50]D), with a mean UCVA of +0.63±0.33 (20/30) and mean BCVA of 0.98±0.22 (20/20). These results are summarized on Table 2 below.

TABLE 2

Summary of pre-refractive, pre-cataract and post-cataract surgery data for myopic group

|  | N | Mean ± s.d | Median | Range |
| --- | --- | --- | --- | --- |
| Pre-LASIK SEQ (D) | 21 | −5.45 ± 2.82 | −5.00 | [−10.37]-[−1.25] |
| Post LASIK SEQ (D) | 21 | −0.23 ± 0.90 | 0.00 | [+1.25]-[−3.62] |
| Pre-Cat SEQ (D) | 21 | −1.88 ± 1.59 | −1.25 | [−5.13]-[+1.25] |
| Pre-CE BCVa | 21 | 0.59 ± 0.20 | 0.66 | 0.33-1.00 |
| Aim-Post SEQ (D) | 21 | +1.48 ± 2.09 | 1.41 | [−2.28]-[+6.30] |
| Post CE SEQ (D) | 21 | +0.03 ± 2.44 | −0.12 | [−3.12]-[+7.50] |
| Post-CE UCVa | 21 | 0.63 ± 0.33 | 0.66 | 0.05-1.00 |
| Post-CE BCVa | 21 | 0.98 ± 0.22 | 1.00 | 0.50-1.33 |

For the hyperopic group, the mean SEQ prior to refractive surgery was +3.07±2.50 D (Range [+1.37]−[+7.75]D). The mean SEQ after refractive surgery +0.03±0.92 D (Range [−1.50]−[+1.75]D). The mean SEQ prior to cataract formation was +0.13±1.26 D (Range [−1.87]−[+1.75]D). After cataract development, mean BCVA was 0.64±0.21 (20/30). After cataract surgery, the SEQ was −0.25±1.40D (Range [−2.64]−[+2.17]D) off the aim of the IOL. The mean SEQ after cataract surgery was −0.79±1.87D (Range [−4.17]−[+1.87]D). The mean UCVA after cataract surgery was 0.40±0.29 (20/50) and the mean BCVA was 0.83±0.19 (20/25). These results are summarized on Table 3 below.

TABLE 3

Summary of pre-refractive, pre-cataract and post-cataract surgery data for hyperopic group

|  | N | Mean ± s.d | Median | Range |
| --- | --- | --- | --- | --- |
| Pre-LASIK SEQ (D) | 10 | +3.07 ± 2.50 | 2.00 | [+1.37]-[+7.75] |
| Post LASIK SEQ (D) | 10 | +0.03 ± 0.92 | −0.06 | [−1.50]-[+1.75] |
| Pre-Cat SEQ (D) | 10 | +0.13 ± 1.26 | 0.25 | [−1.87]-[+1.75] |
| Pre-CE BCVa | 10 | 0.64 ± 0.21 | 0.58 | 0.33-1.00 |
| Aim-Post SEQ (D) | 10 | −0.25 ± 1.40 | 0.06 | [−2.64]-[+2.17] |
| Post CE SEQ (D) | 10 | −0.79 ± 1.87 | −0.50 | [−4.17]-[+1.87] |
| Post-CE UCVa | 10 | 0.40 ± 0.29 | 0.35 | 0.05-0.80 |
| Post-CE BCVa | 10 | 0.83 ± 0.19 | 1.00 | 0.40-0.80 |

IOL powers were calculated retrospectively with 6 different methods as described above. The IOL for emmetropia obtained with each method was compared to a theoretical $IOL_{exact}$ which was computed from $K_{exact}$, after an IOL was successfully implanted and a post cataract surgery SEQ was obtained.

For the myopic group, FIG. 1 shows the average deviation of each method from emmetropia. Method I, or clinical history method ($IOL_{HisK}$), had a mean deviation from $IOL_{exact}$ of −1.76±1.76D (Range: [−5.72]−[+1.79]D). Method II, or clinical history method on spectacle plane ($IOL_{HisKs}$), had a mean deviation of −0.56±1.59D (Range: [−4.28]−[+3.38]D). Method III, or vertex method ($IOL_{vertex}$), had mean deviation of 1.51±1.95D (Range: [−1.78]−[+5.42]D). Method IV, or back calculated method ($IOL_{BC}$), had a mean deviation 1.06±1.51D (Range: [−1.56]−[+5.13]D). $IOL_{avgK}$ had a mean deviation of −2.32±2.36 D (Range: [−9.46]−[+2.17]D) and $IOL_{flatK}$ had a mean deviation of −1.72±2.19 (Range: [−8.57]−[1.33]D). Table 4 shows the percentage deviation of each method of IOL calculation from $IOL_{exact}$ for myopic eyes. Only $IOL_{HisKs}$ showed no statistical difference when compared to $IOL_{exact}$ −(0.47x+0.85), and for $IOL_{avgK}$ the adjustment would be −(0.46x+0.21), where x=pre-refractive surgery $SEQ_m$. These graphs are shown in FIG. 2. A clinical example will be shown below.

Figure 4:
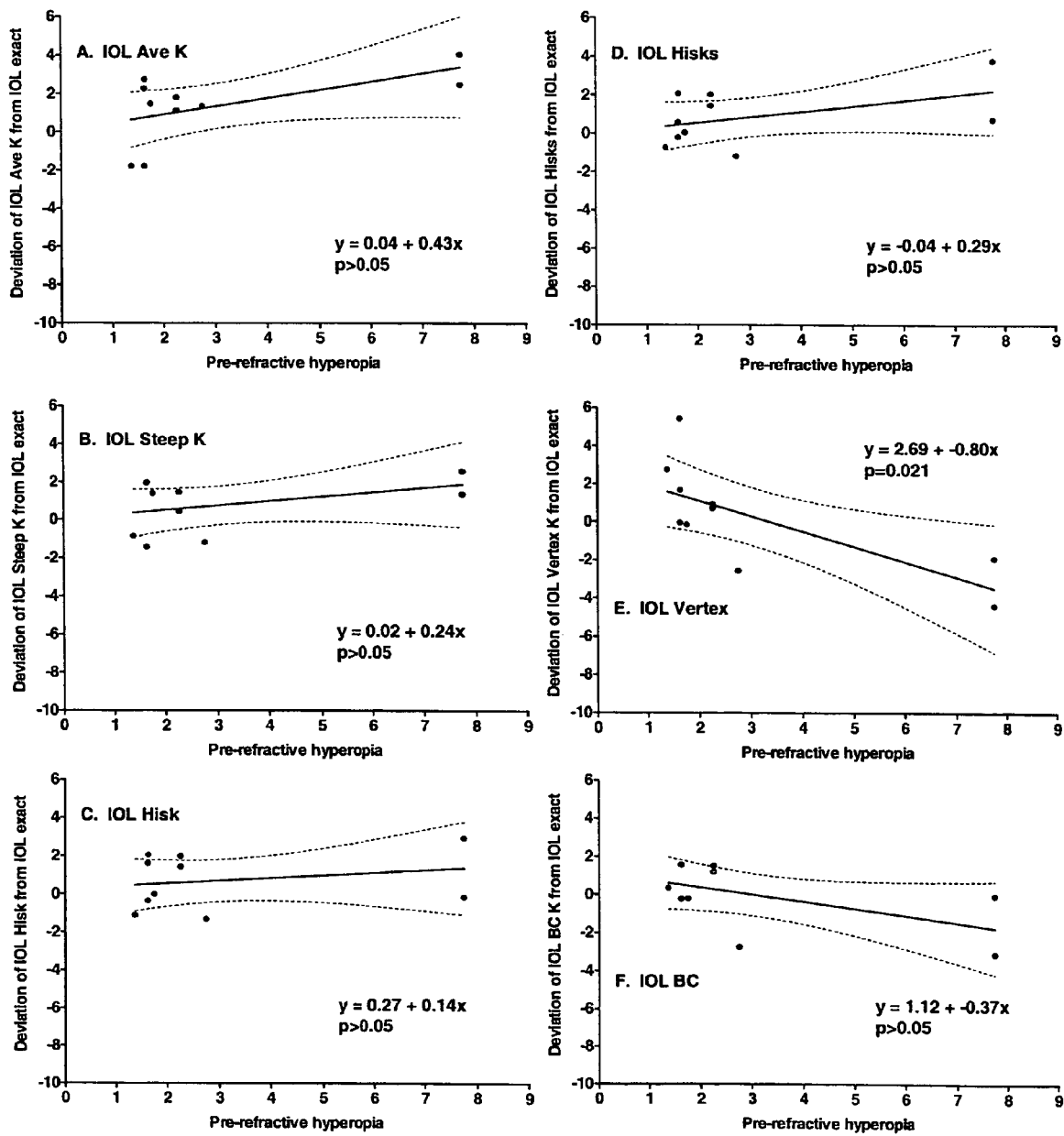

For the hyperopic group similar analysis was performed and shown on FIG. 4. Each method had the following deviations from $IOL_{exact}$: $IOL_{HisK}$ +0.70±1.47D (Range [−1.31]−[+2.94]D), $IOL_{HisKs}$ +0.84±1.50D (Range [−1.20]−[+3.75D]

TABLE 4

Percentage of deviation of each method IOL calculation in myopic eyes

| | | IOL power measurement† | | | IOL power change percentage‡ | | |
|---|---|---|---|---|---|---|---|
| | N | Mean ± s.d. | Median | Range | Mean ± s.d. | Median | Range |
| IOL exact | 21 | 19.35 ± 2.20 | 19.03 | 15.64–24.73 | — | — | — |
| IOL Avg K | 21 | 17.03 ± 2.54 | 17.00 | 11.54–22.05 | −11.6 ± 11.7 | −11.6 | −45.1–13.3 |
| IOL Flat K | 21 | 17.63 ± 2.46 | 17.63 | 12.43–22.62 | −8.5 ± 10.7 | −9.1 | −40.8–8.1 |
| IOL HisK | 21 | 17.59 ± 2.30 | 17.86 | 13.60–24.33 | −8.8 ± 9.1 | −10.4 | −27.2–10.9 |
| IOL HisKs | 21 | 18.79 ± 2.33 | 18.60 | 15.09–24.50 | −2.6 ± 8.6 | −3.4 | −20.4–20.7 |
| IOL Vertex | 21 | 20.86 ± 2.46 | 21.10 | 15.63–26.49 | 8.2 ± 10.8 | 7.1 | −10.2–32.0 |
| IOL BC | 21 | 20.41 ± 2.19 | 20.25 | 15.85–25.80 | 5.9 ± 8.7 | 6.4 | −9.0–31.3 |

†Paired-test indicated that mean difference between each of methods and IOL exact value was significantly different (p < 0.01), but the difference between IOL HisKs and IOL exact value was not statistically significant.
‡The IOL power change percentage was calculated by (the value of each of methods − IOL exact value) ÷ IOL exact value × 100.

Linear regression was performed on this group which looked at each method compared to pre-refractive surgery $SEQ_m$. Of the six methods only $IOL_{flatK}$ (p=0.0036) and $IOL_{avgK}$ (p=0.0094) showed statistically significant trends. Based on these results, the amount of underestimation for $IOL_{flatK}$ and $IOL_{avgK}$ could be predicted if the pre-refractive surgery $SEQ_m$ is known. For $IOL_{flatK}$ the adjustment would be D), $IOL_{vertex}$ +0.24+2.80D (Range [−4.41]−[+5.43]D), $IOL_{BC}$ −0.02±1.70D (Range [−3.13]−[+1.57]D), $IOL_{avgK}$ +1.36±1.86D (Range [−1.80]−[+4.03]D) and $IOL_{steepK}$+ 0.75±1.44D (Range [−1.44]−[2.57]D). Table 5 shows percentage deviation of each method of IOL calculation from $IOL_{exact}$ for hyperopic eyes, only $IOL_{BC}$ and $IOL_{vertex}$ showed no statistical difference to $IOL_{exact}$.

TABLE 5

Percentage of deviation of each method IOL calculation in hyperopic eyes.

| | | IOL power measurement† | | | IOL power change percentage‡ | | |
|---|---|---|---|---|---|---|---|
| | N | Mean ± s.d. | Median | Range | Mean ± s.d. | Median | Range |
| IOL exact | 10 | 20.20 ± 2.79 | 20.64 | 15.18–24.63 | — | — | — |
| IOL Avg K | 10 | 22.72 ± 2.39 | 22.18 | 19.47–27.10 | 13.2 ± 8.3 | 10.9 | 5.4–32.6 |
| IOL Steep K | 10 | 21.89 ± 2.18 | 21.27 | 19.02–25.98 | 9.2 ± 9.2 | 8.3 | −5.5–29.6 |
| IOL HisK | 10 | 21.85 ± 1.90 | 21.15 | 19.30–24.75 | 9.3 ± 11.1 | 9.0 | −6.0–33.8 |
| IOL HisKs | 10 | 21.87 ± 2.34 | 21.14 | 19.01–25.56 | 9.3 ± 11.6 | 8.1 | −5.5–34.1 |
| IOL Vertex | 10 | 20.34 ± 1.33 | 20.37 | 18.29–22.96 | 2.3 ± 14.7 | 1.5 | −17.9–35.2 |
| IOL BC | 10 | 20.78 ± 1.57 | 20.95 | 18.65–23.75 | 4.4 ± 14.4 | 2.8 | −12.7–37.7 |

†Paired-test indicated that mean difference between each of methods and IOL exact value was significantly different (p < 0.05), but the differences between IOL Vertex and IOL exact value and that between IOL BC and IOL exact value were not statistically significant.
‡The IOL power change percentage was calculated by (the value of each of methods − IOL exact value) ÷ IOL exact value × 100.

Linear regression was performed on this group as well, comparing each methods' trend to pre-refractive surgery $SEQ_h$. Of this group only $IOL_{vertex}$ showed statistical significance (p=0.021). Based on this result the amount adjustment of $IOL_{vertex}$ method in the hyperopic group could be predicted by the following formula: −(−0.80x+2.69), where x=pre-refractive surgery $SEQ_h$ (FIG. 3).

Although the present invention has been described in detail with particular reference to preferred embodiments thereof, it should be understood that the invention is capable of other different embodiments, and its details are capable of modifications in various obvious aspects. As is readily apparent to those skilled in the art, variations and modifications can be affected while remaining within the spirit and scope of the invention. Accordingly, the foregoing disclosure, description, and figures are for illustrative purpose only, and do not in any way limit the invention which is defined only by the claims.

REFERENCES

1. Argento C J, Cosentino M J. Laser in situ keratomileusis for hyperopia. J Cataract Refract Surg 1998; 24: 1050-1058.
2. Holladay J T. Cataract surgery in patients with previous keratorefractive surgery (RK, PRK, and LASIK). Ophthalmic Practice 1997; 15: 238-244.
3. Zeh W G, Koch D D. Comparison of contact lens over refraction and standard keratometry for measuring corneal curvature in eyes with lenticular opacity. J Cataract Refract Surg 1999; 25: 898-903.
4. Celikkol L, Pavlopoulos G, Weinstein B, et al. Calculation of intraocular lens power after radial keratotomy with computerized videokeratography. Am J Ophthalmol 1995; 120: 739-750.
5. Alimisi S, Miltsakakis D, Klyce S. Corneal topography for intraocular lens power calculations. J Refract Surg 1996; 12: S309-S311.
6. Cuaycong M J, Gay C A, Emery J, et al. Comparison of the accuracy of computerized videokeratography and keratometry for use in intraocular lens power calculations. J Cataract Refract Surg 1993; 19: 178-181.
7. Husain S E, Kohnen T, Maturi R, et al. Computerized videokeratography and keratometry in determining intraocular lens calculations. J Cataract Refract Surg 1996; 22: 362-366.
8. Hamed A M, Wang L, Misra M, Koch D D. A comparative analysis of five methods of determining corneal refractive power in eyes that have undergone myopic laser in situ keratomileusis. Ophthalmology 2002; 109: 651-658.
9. Argento C, Cosentino M J, Badoza D. Intraocular lens power calculation after refractive surgery. J Cataract Refract Surg 2003; 29: 1346-1351.
10. Seitz B, Torres F, et al. Posterior corneal curvature changes after myopic laser in situ keratomileusis. Ophthalmology 2001, 108: 666-673.
11. Speicher L. Intra-ocular lens calculation status after corneal refractive surgery. Curr Opinion Ophthalmol. 2001; 12: 17-29.
12. Odenthal M P, Eggink C A, et al. Clinical and theoretical results of intraocular lens power calculation for cataract surgery after photorefractive keratectomy for myopia. Arch Ophthalmol. 2002: 120: 431-438.
13. Feiz V, Mannis M J, et al. Intraocular lens power calculation after laser in situ keratomileusis for myopia and hyperopia. Cornea 2001, 20: 792-797.
14. Hamilton D R, Hardten D R. Cataract surgery in patients with prior refractive surgery. Current Opinion in Ophthalmology 2003; 14: 44-53.
15. Kim J H, Lee D H, Joo C K. Measuring corneal power for intraocular lens power calculation after refractive surgery. J Cataract Refract Surg. 2002; 28: 1932-1938.
16. Randleman J B, et al. Intraocular Lens Power Calculations after Laser In Situ Keratomileusis. Cornea. 2002; 21 (8): 751-755.
17. Stakheev A A, Balashevich L J. Corneal Power Determination After Previous Corneal Refractive Surgery for Intraocular Lens Calculation. Cornea. 2003; 22: 214-220.
18. Ladas J G, Wachler B S B, Hunkerler J D, Durrie D S. Intraocular Lens Power Calculations Using Corneal Topography After Photorefractive Keratectomy. American Journal of Ophthalmology. 2001; 132: 254-255.
19. Gimbel H V, Sun R. Accuracy and predictability of intraocular lens power calculation after laser in situ keratomileusis. J Cataract Refract Surg. 2001; 27: 571-576.
20. Kalski R S, et al. Intraocular Lens Power Calculation for Cataract Surgery after Photorefractive Keratectomy for High Myopia. J Refract Surg. 1997; 13: 362-366.
21. Gimbel H V, et al. Accuracy and predictability of intraocular lens power calculation after photorefractive keratectomy. J Cataract Refract Surg. 2000; 26: 1148-1151.
22. Seitz B, Langenbucher A. Intraocular lens calculations status after corneal refractive surgery. Current Opinion in Ophthalmology. 2000; 11: 35-46.
23. Lesher M P, et al. Phacoemulsification with intraocular lens implantation after excimer photorefractive keratectomy: A case report. J Cataract Refract Surg. 1994; 20: 265-267.
24. Morris A H, Corbett M. Errors in intraocular lens power calculation after photorefractive keratectomy. Eye. 1998; 12: 327-328.
25. Holladay J T. Consultations in refractive surgery. Refract Corneal Surg. 1989; 5: 203.
26. Guyton D L. Consultations in refractive surgery. Refract Corneal Surg. 1989; 5: 203.

What is claimed is:

1. A method of determining an intraocular lens (IOL) power for an aphakic eye, comprising the steps of:
    a) determining a required IOL power to provide a desired refraction;
    b) determining a pre-refractive surgery spherical equivalent (SEQ) of the aphakic eye;
    c) determining an IOL ($IOL_{exact}$) based on the result of (b); and
    d) adjusting the calculated power obtained from (a) by subtracting from it a value comprising x(SEQ)+y, wherein x and y are slope and intercept constants respectively derived from regression analysis of the relationship of SEQ to the deviation of the calculated IOL power from $IOL_{exact}$, wherein the adjusted power is the IOL power for the aphakic eye.

2. The method of claim 1, wherein the aphakic eye is an aphakic myopic eye.

3. The method of claim 2, wherein the required IOL power is calculated using flattest keratometry reading.

4. The method of claim 3, wherein the value of x is between 0.4 and 0.6 and the value of y is between 0.75 and 0.85.

5. The method of claim 4, wherein the value of x is 0.47 and the value of y is 0.8.

6. The method of claim 2, wherein the required IOL power is calculated using average keratometry reading.

7. The method of claim 6, wherein the value of x is between 0.4 and 0.6 and the value of y is between 0.5 and 1.0.

8. The method of claim 7, wherein the value of x is 0.46 and the value of y is 0.21.

9. The method of claim 1, wherein the aphakic eye is an aphakic hyperopic eye.

10. The method of claim 9, wherein the value of x is between 0.6 and 1.0 and the value of y is between 1.7 and 3.7.

11. The method of claim 10, wherein the value of x is 0.8 and the value of y is 2.69.

12. A calculating device employing the method of claim 1 to determine an IOL power for an aphakic eye.

13. The device of claim 12, wherein input to the device comprises keratometry values of the eye and pre-refractive surgery spherical equivalent of the eye, and output from the device comprises a corrected IOL power for an aphakic eye.

14. The device of claim 12, wherein the device is a mechanical calculating device.

15. The device of claim 12, wherein the device is an electronic calculating device.

16. The device of claim 15, wherein the electronic device uses a computer program to determine the IOL power for an aphakic eye.

* * * * *